US008415266B2

(12) United States Patent
Eckhardt et al.

(10) Patent No.: US 8,415,266 B2
(45) Date of Patent: Apr. 9, 2013

(54) CATALYST CONSTITUENT

(75) Inventors: Gunther Eckhardt, Bad Duerrenberg (DE); Erich Wanek, Kaufering (DE); Bernd Kuppermann, Herrsching (DE)

(73) Assignee: 3M Deutschland GmbH, Seefeld (DE)

(*) Notice: Subject to any disclaimer, the term of this patent is extended or adjusted under 35 U.S.C. 154(b) by 0 days.

(21) Appl. No.: 10/257,760

(22) PCT Filed: Apr. 12, 2001

(86) PCT No.: PCT/EP01/04217
§ 371 (c)(1),
(2), (4) Date: Dec. 12, 2002

(87) PCT Pub. No.: WO01/79328
PCT Pub. Date: Oct. 25, 2001

(65) Prior Publication Data
US 2003/0153726 A1    Aug. 14, 2003

(30) Foreign Application Priority Data
Apr. 17, 2000   (DE) .................................. 100 18 918

(51) Int. Cl.
*B01J 31/00*       (2006.01)
*C08G 18/48*       (2006.01)

(52) U.S. Cl.
USPC .......................................... 502/150; 521/99

(58) Field of Classification Search .................. 502/150; 523/109; 525/533; 521/99
See application file for complete search history.

(56) References Cited

U.S. PATENT DOCUMENTS

| | | | |
|---|---|---|---|
| 3,453,242 A | | 7/1969 | Scmitt et al. |
| 3,735,007 A | | 5/1973 | Lapidus et al. |
| 3,842,019 A | | 10/1974 | Kropp |
| 4,038,113 A * | | 7/1977 | Oberth .......................... 149/19.4 |
| 4,122,038 A * | | 10/1978 | Sandner et al. ............... 502/155 |
| 4,268,310 A * | | 5/1981 | Nemeth ...................... 106/38.35 |
| 4,369,122 A * | | 1/1983 | Schubart et al. ............... 502/167 |
| 4,431,421 A * | | 2/1984 | Kawahara et al. ............. 523/115 |
| 4,691,045 A * | | 9/1987 | Fukuchi et al. ............... 560/185 |
| 4,891,400 A * | | 1/1990 | Schwabe et al. .............. 524/745 |
| 5,015,413 A * | | 5/1991 | Nagaoka .......................... 252/511 |
| 5,234,964 A * | | 8/1993 | Lin et al. ......................... 521/99 |
| 5,502,144 A * | | 3/1996 | Kuo et al. ........................ 528/18 |
| 5,595,487 A * | | 1/1997 | Ario et al. ...................... 433/226 |
| 5,656,703 A * | | 8/1997 | Costin et al. .................. 525/531 |
| 5,792,821 A * | | 8/1998 | Bowen ........................ 526/238.2 |
| 5,925,723 A * | | 7/1999 | Friebe et al. .................... 528/18 |
| 5,945,466 A * | | 8/1999 | Ikeno et al. .................... 523/109 |
| 5,981,740 A * | | 11/1999 | Bowen ........................... 536/103 |
| 6,057,380 A * | | 5/2000 | Birbaum et al. .................. 522/8 |
| 6,075,068 A * | | 6/2000 | Bissinger ...................... 523/116 |
| 6,084,004 A * | | 7/2000 | Weinmann et al. ............. 522/25 |
| 6,180,739 B1 * | | 1/2001 | Bowen ........................ 526/238.2 |
| 6,218,461 B1 * | | 4/2001 | Schwabe et al. ............... 524/588 |
| 6,232,361 B1 * | | 5/2001 | Laksin et al. ...................... 522/84 |
| 6,281,307 B1 * | | 8/2001 | Muhlebach et al. ........... 526/171 |
| 6,291,546 B1 * | | 9/2001 | Kamohara et al. ............. 523/109 |
| 6,383,279 B1 * | | 5/2002 | Eckhardt et al. .............. 106/38.2 |
| 6,503,994 B1 * | | 1/2003 | Nehren et al. ................... 528/17 |
| 6,541,657 B2 * | | 4/2003 | Abe et al. ....................... 560/209 |
| 6,583,248 B1 * | | 6/2003 | Bowen ........................ 526/238.2 |
| 6,599,960 B1 * | | 7/2003 | Eckhardt et al. .............. 523/109 |
| 6,610,759 B1 * | | 8/2003 | Chappelow et al. ............ 522/25 |
| 6,686,330 B2 * | | 2/2004 | Jordan et al. .................. 510/475 |
| 6,767,980 B2 * | | 7/2004 | Yurugi et al. .................. 526/320 |
| 6,794,481 B2 * | | 9/2004 | Amagai et al. ................ 528/219 |
| 6,835,785 B2 * | | 12/2004 | Ishii et al. ...................... 525/391 |
| 6,841,111 B2 * | | 1/2005 | Rickner et al. ................ 264/250 |
| 6,855,785 B2 * | | 2/2005 | Baumgart et al. ............. 526/194 |
| 6,867,246 B2 * | | 3/2005 | Nowak et al. ................. 523/109 |
| 6,906,117 B2 * | | 6/2005 | Nowak et al. ................. 523/109 |

FOREIGN PATENT DOCUMENTS

| | | |
|---|---|---|
| DE | 197 53 456 A1 | 6/1999 |
| DE | 197 53 461 A1 | 6/1999 |
| EP | 0 279 238 A1 | 8/1988 |
| EP | 001277777 A2 * | 1/2003 |

OTHER PUBLICATIONS

"Environmental Coatings Glossary" [online]. EnviroTech Financial, Inc., Orange, CA, 2002-2008 [retrieved on Oct. 17, 2008]. Retrieved from the Internet<URL:http://www.etfinancial.com/coatingsgloss. htm>; 9 pgs.

Grant et al., *Grant & Hackh's Chemical Dictionary*, McGraw-Hill Book Company, New York, NY; title page, publisher's page, and pp. 303 and 187 only.

"Zinsser Glossary of Painting Related Terms" [online]. Zinsser Co., Inc., Somerset, NJ, 2003 [retrieved on Oct. 17, 2008]. Retrieved from the Internet:<URL:http://www.zinsser.com/glossary.asp?letter=R>; 3 pgs.

* cited by examiner

*Primary Examiner* — Aileen B Felton
(74) *Attorney, Agent, or Firm* — Carlos M. Téllez; 3M Deutschland GmbH

(57) ABSTRACT

The invention relates to catalyst components, containing:
  (A) at least one Brönsted acid,
  (B) water,
  (C) at least one antacid-acting compound from the group consisting of the oxides, hydroxides, carbonates and/or carboxylates of the elements aluminum, chromium, copper, germanium, manganese, lead, antimony, tin, tellurium, titanium and/or zinc,
  (D) optionally at least one inert diluent,
  (E) optionally at least one modifier,
the mixture of one part by weight of the catalyst component with three parts by weight bisaziridino polyether with an average imino equivalent mass of 3100, preparable from a polyetherdiol which comprises ethylene oxide and tetrahydrofuran units in the molar ratio 1:3.5 solidifying within 0.5 to 20 minutes to a solid elastomer material which has a shore A hardness of at least 20 according to DIN 53505 after 24 hours' storage time at room temperature.

28 Claims, No Drawings

CATALYST CONSTITUENT

This application is the national phase under 35 U.S.C. §371 of PCT International Application No. PCT/EP01/04217 which has an International filing date of Apr. 12, 2001, which designated the United States of America.

The invention relates to preparations based on aziridino polyethers which cure through polymer-forming reactions after mixing of two separately stored components. The invention describes in particular such preparations which are characterized by a well adjustable, relatively long processing time after completed mixing and a low acidity of the catalyst component.

For the use of two-component preparations based on aziridino-group-containing compounds it is important to be able to adjust the pattern of the degree of conversion/time curve according to the respective requirements.

Two characteristic values in particular of this curve pattern interest the user: the processing time and the time until further processability of the cured materials is achieved.

By processing time is meant in this case the period between complete mixing of the two components and the incipient curing of the mixed preparation at room temperature. This polymerization start is regarded as the time at which a mixed two-component preparation passes from the plastic phase into the elastic phase and displays pronounced changes such as skin formation, cobwebbing and greatly reduced flowability.

The mixed preparation can still be processed until shortly before this time and displays the required flow-on behaviour on the respective substrates.

The user normally desires a processing time of approx. 0.5 to 4 minutes at room temperature in order to have enough time to be able to carry out the possibly multiple positioning and dosing of the cured material and corrective measures. In this case, the establishment of long processing times proves particularly difficult.

The demand for long processing times is mostly associated with the desire to make possible the further processability of the cured material after as short a period of time as possible.

For a particularly important application of dental modelling with two-component preparations based on aziridino-group-containing compounds, this means that:

Processing times of 2 to 4 minutes at room temperatures are to be achieved, and the further processability of the model in less than 7 minutes after the end of mixing is to be guaranteed. By further processing is meant for example in dentistry the removal of the cured impression from the patient's mouth. This must not take place too soon as otherwise the precision of the impression is damaged by the material which is not yet completely set.

An important requirement is furthermore that the formulation changes which make possible the described characteristics of the chronological setting pattern must not have a negative influence on important properties of the cured elastic materials.

The establishment of the chronological setting pattern takes place in the case of two-component preparations based on aziridino polyethers through the initiation system, i.e. through interaction of suitably selected starters and retarders.

It has been known for a long time that N-alkylaziridino compounds can cure when exposed to the action of acid-acting compounds (H. Bestian, Methoden der Organischen Chemie (Houben-Weyl), XII/1 (1958)).

A summary of the starter substances used for the curing of N-alkylaziridino compounds is contained in O. C. DERMER, G. E. HAM "Ethylenimine and other Aziridines" Academic Press (1969).

Accordingly, a large number of compound classes and compounds have proved to be suitable starters in principle.

However the selection of starters which can actually be used for medical dental and technical dental impression materials is strictly limited by a range of additional requirements. Thus no unpleasant-smelling compounds may form during curing. Furthermore, in the preparation, filling and dosing of the catalyst components, no corrosion phenomena should occur on metal parts and plastic parts in contact with the product. In addition no skin irritations are to occur on the staff or on the patient, even in the case of improper storage and also use of the unmixed components and in particular the catalyst components not in accordance with the regulations.

Storage-stable, cationically polymerizable preparations with improved curing behaviour based on N-alkylaziridino-group-containing compounds which contain soluble and/or fine-particle alkaline-earth and/or alkali metal compounds to increase storage stability are known from DE-A-197 53 461. These can be added both to the catalyst component and the base component, the addition to the base component being the preferred version.

Furthermore it is known from DE-A-197 53 456 that the processing time of cationically cured preparations based on aziridino polyethers can be adjusted as desired by the addition of alkali or alkaline-earth compounds as setting-retarding additives. The alkali or alkaline-earth compounds are incorporated into the base paste in both dissolved and in fine-particle, solid form.

The disadvantage of the compositions described above is that the acid used as catalyst can lead to irritations or cauterizations on the patient, and corrodes and damages the bags, provided with a metal coating, in which the base and catalyst component are packed. These disadvantages occur regardless of whether the alkali or alkaline-earth compounds are present in the base paste as stipulated in DE-A-197 53 456, or whether they are present in the base or in the catalyst paste in accordance with DE-A-197 53 461.

The object of the invention is therefore the preparation of catalyst components for two-component preparations based on N-alkylaziridino-group-containing compounds, these catalyst components guaranteeing an easily reproducible establishment of the setting pattern and the resulting properties, and also effecting, in unmixed state, no irritation, cauterization, corrosion or damage to the packaging.

The object is achieved by catalyst components, containing:
(A) at least one Brönsted acid,
(B) water
(C) at least one antacid-acting compound from the group consisting of the oxides, hydroxides, carbonates and/or carboxylates of the elements aluminium, chromium, copper, germanium, manganese, lead, antimony, tin, tellurium, titanium and/or zinc,
(D) optionally at least one inert diluent,
(E) optionally at least one modifier, the mixture of one part by weight of the catalyst component with three parts by weight bisaziridino polyether with an average imino equivalent mass of 3100, preparable from a polyetherdiol which comprises ethylene oxide and tetrahydrofuran units in the molar ratio 1:3.5 solidifying within 0.5 to 20 minutes to a solid elastomer material which has a Shore A hardness of at least 20 according to DIN 53505 after 24 hours' storage time at room temperature.

The times given here are not to be understood as processing time or time of further processability within the meaning of the foregoing. The solidifying times to be achieved within the meaning of a test system are involved.

The bisaziridino polyether used as test substance for the catalyst component is syntheticized from a polyetherdiol which is accessible by cationic copolymerization of ethylene oxide and tetrahydrofuran under catalytic action of boron trifluoride etherate, a molar incorporation ratio of ethylene oxide to tetrahydrofuran of 1:3.5 being set through the reaction process, by reaction with crotonic anhydride and subsequent addition of ethylene imine, as shown in U.S. Pat. No. 3,453,242, Example 13.

The constituents of the catalyst components are preferably defined as follows:
- (A) 0.1 to 50 wt.-%, preferably 1 to 20 wt.-% at least one Brönsted acid,
- (B) 0.1 to 20 wt.-%, preferably 0.5 to 10 wt.-% water,
- (C) 0.1 to 50 wt.-%, preferably 0.5 to 10 wt.-% at least one of the named antacid-acting compounds;
- (D) 0 to 95 wt.-%, preferably 0 to 70 wt.-% at least one inert diluent,
- (E) 0 to 50 wt.-%, preferably 0 to 30 wt.-% modifiers, including fillers, dyes, pigments, thixotropic agents, flow improvers, polymeric thickeners, surfactants, odorous substances and flavourings, and compounds retarding polymer formation, the wt.-% data being related in each case to the overall mass of the catalyst component.

It is surprising that through the use of antacid-acting compounds in Brönsted-acid-containing catalyst components, despite the very greatly reduced acidity, a sufficiently rapid curing of the admixed preparation can be achieved, that the processing time of these preparations can be established in the desired range via the water concentration, and that the catalyst component according to the invention does not cause irritations or cauterizations and also does not corrode the packaging (bags coated with metal).

A large number of compound classes and acid compounds can be considered for use as acid according to constituent (A).

In principle both organic and inorganic acids are suitable. The speed of the curing reaction also displays in addition to other dependences a clear dependence on the strength of the acid. Thus very strong acids such as hexafluoroantimonic acid, hexafluorophosphoric acid or tetrafluoroboric acid are characterized by high speeds of cationic polymerization. High reaction speeds are also achieved by sulphonic acids such as 4-toluenesulphonic acid, 4-phenolsulphonic acid, 4-bromobenzenesulphonic acid, 4-chlorobenzenesulphonic acid, benzenesulphonic acid, alkylbenzenesulphonic acids, in particular dodecylbenzenesulphonic acid, naphthalene-2-sulphonic acid and alkanesulphonic acids. The use of phosphonic acids such as vinylphosphonic acid and propylphosphonic acid is also possible.

The use of polymeric acids such as polyvinylphosphonic acid, polyacrylic acid, copolymeric acids, prepared from maleic anhydride with other monomers, is also possible, if a storage-stable distribution state of these polymers in the catalyst component is achieved.

Furthermore, saturated and unsaturated carboxylic acids such as propionic acid, succinic acid, tartaric acid, trimellitic acid, benzoic acid, phenylacetic acid, citric acid, maleic acid, adipinic acid, o-chlorobenzoic acid or reaction products of polyvalent alcohols and acid anhydrides such as maleic anhydride and succinic anhydride can also be used.

The preparations according to the invention contain as constituent (A) at least one acid; the use of several acids is possible and can be expedient to adjust the setting process.

The water used according to constituent (B) can either be added to the acids or be added to the preparation at a later time in the preparation of the catalyst component.

The use of water-containing acids as constituent (A) is preferred, the adjustment of the concentration to the desired value being able to be carried out in the course of the preparation of a preliminary solution.

The water quantity depends on the solubility of the acids in the further constituents of the catalyst component, the desired curing pattern and further properties of the catalyst component and the cured impression material.

To achieve a better solubility of the Brönsted acid in the catalyst component it is however expedient to add the greater part of the water required to the catalyst component.

The oxides, hydroxides, carbonates and carboxylates of the elements aluminium, chromium, copper, germanium, manganese, lead, antimony, tin, tellurium, titanium and zinc are used as antacid-acting compounds within the meaning of the invention corresponding to constituent (C). The use of aluminium and zinc compounds is preferred.

Zinc compounds such as zinc hydroxide, zinc oxide, zinc carbonate or mixtures of these compounds are particularly advantageously used.

The ratio between constituents (A) and (C) can vary greatly. It has however proved to be advantageous to use 0.5 to 2.0 base equivalent from constituent (C) on an acid equivalent from constituent (A). A ratio of an acid equivalent to 0.7 to 1.2 base equivalent is particularly preferred.

Polyether polyols such as polypropylene glycols or mixed polyetherols with tetrahydrofuran and/or ethylene oxide and/or propylene oxide units, polyester polyols such as polycaprolactone diols and polycaprolactone triols, polycarbonate diols, aliphatic esters, oils, fats, waxes, aliphatic hydrocarbons, araliphatic hydrocarbons and mono- or multifunctional esters of polyvalent acids such as phthalic acid or citric acid or esters or amides of alkylsulphonic acid and arylsulphonic acids are used as inert diluent corresponding to constituent (D).

Modifiers can be added to the catalyst component as constituent (E). These comprise fine-particle fillers such as alumosilicates, silicic acids, quartz powder, wollastonite, mica powder and diatomaceous earth as well as dyes and pigments the addition of which makes possible a better assessment of the mixing quality and reduces the danger of confusion, thixotropic agents such as finely-dispersed silicic acids and other additives influencing the flow behaviour, such as polymeric thickeners, furthermore surfactants for establishing the flow-on behaviour and also odorous substances and/or flavourings.

The required water concentration in the cured preparation can be ascertained through tests, at least a part of the required water being able to be present also in the base component before mixing.

The suitable concentrations of water and antacid-acting compounds can be ascertained by a simple test.

The base component can only consist of aziridino monomers as described for example as test substance for the catalyst component.

To establish an improved handling and to achieve the desired property combination of the elastomer material the base component can contain:
- (I) 5 to 100 wt.-% at least one N-alkylaziridino compound with aziridino equivalent masses of 500 to 25,000 g/equivalent, (II) 0 to 95 wt.-% at least one inert diluent,
(III) 0 to 80 wt.-% modifiers.

The two components are stored separately and for processing are mixed together in a ratio of catalyst component to base component of 5:1 to 1:20, preferably 1:1 to 1:10.

The preparation of the catalyst components according to the invention can take place in different ways.

Thus the Brönsted acid can be dissolved together with water at 20° C. to 90° C., preferably 50° C. to 70° C. in a part or the total quantity of the inert diluent according to constituent (D) and the antacid-acting compound added as powder, as paste or as suspension before or after the incorporation of fillers and dyes.

According to a preferred version of the catalyst component preparation a paste is prepared from constituents (A), (B), (D) and (E) and the antacid-acting compounds (C) then added, it being particularly preferred to use the antacid-acting compounds in the form of a paste or a suspension each of which was prepared from a part of the diluent and the antacid-acting compounds.

The catalyst components according to the invention for two-component preparations cured by polymer-forming reactions based on N-alkylaziridino compounds can be used, depending on the composition of the catalyst component and the base component, for the gluing of substrates, for sealing, coating and casting.

The dosing of the two components can be carried out by sight (strand-length comparison), by weight, via pre-dosed pack units and subsequent manual admixing, from double-chambered cartridges with static mixing tube or by means of volume dosing systems with downstream static or dynamic mixers.

A high mixing quality is required to achieve optimum results. On the other hand, the tolerance of the mixing ratio is in general relatively high and can for example cover the range 0.8 to 1.2:5, with a preset catalyst component to base component ratio of 1:5, without use-restricting property changes being ascertained.

The preparations according to the invention can advantageously be used for the modelling of objects or body parts, models with accurate details being obtained with the preparations according to the invention due to their excellent flow-on behaviour.

The preparations according to the invention are used to particular advantage in medical dental and technical dental modelling.

In medical dental modelling the good flow-on behaviour on the moist tooth and the moist gum as well as the insensitivity of the precision of the modelling vis-à-vis saliva and blood proves to be of great advantage.

A further subject of the invention are packages and mixing devices containing the materials prepared from the preparations according to the invention, in particular dental materials such as cartridges, bags, dental trays, static and dynamic mixers or mixing apparatuses.

The invention is described in more detail by the following examples.

EXAMPLES

With the help of laboratory kneaders the catalyst components described in Table 1 were prepared on 100-g scale.

In this case, the acids (A) were dissolved in water (B), 70% of the stated diluent (D) was added and the filler (E) was kneaded in and then the suspension of the antacid-acting compounds (C) added in 30% of the stated diluent quantity (D).

The preparation of the base component, the composition of which is given in Table 3, was carried out on 500-g scale.

Table 4 lists the mixtures which were examined using the catalyst components described in Table 1 and the base components described in Table 3, in the weight ratio indicated in each case. The mixtures were prepared by spatula-mixing on the mixing block within 30 seconds and used to determine the properties listed in Table 4.

The mouth-removal time was able to be determined as the average value of each of 3 impressions from 3 different subjects in the form of a complete upper-jaw impression.

The preparation of bisaziridino polyethers from polyetherdiols which are syntheticized by copolymerization of ethylene oxide and tetrahydrofuran is described in principle in Example 13 of U.S. Pat. No. 3,453,242.

The bisaziridino polyether used as test substance for the catalyst component is syntheticized from a polyetherdiol which is accessible by cationic copolymerization of ethylene oxide and tetrahydrofuran under catalytic action of boron trifluoride etherate, a molar incorporation ratio of ethylene oxide to tetrahydrofuran of 1:3.5 being set through the reaction process, by reaction with crotonic anhydride and subsequent addition of ethylene imine, as shown in U.S. Pat. No. 3,453,242, Example 13.

TABLE 1

Composition of the catalyst components according to the invention

| | Constituent | Wt.-% | | | | | | | | | |
|---|---|---|---|---|---|---|---|---|---|---|---|
| | | K1 | K2 | K3 | K4 | K5 | K6 | K7 | K8 | K9 | K10 |
| (A) | p-toluenesulphonic acid monohydrate | 10.1 | 9.9 | 10.0 | 6.7 | 4.1 | 6.0 | 8.9 | 9.8 | 8.3 | 7.3 |
| | tetrafluoroboric acid | — | — | — | 1.2 | 2.7 | — | — | — | — | — |
| | $C_{15}$-n-alkanesulphonic acid | — | — | — | — | — | 3.2 | 1.0 | — | — | 0.2 |
| (B) | distilled water | 5.5 | 4.7 | 3.7 | 5.9 | 5.0 | 5.5 | 6.1 | 4.3 | 3.9 | 5.7 |
| (C) | zinc oxide | 2.0 | 2.0 | 2.0 | 1.9 | 1.5 | 1.6 | 1.9 | — | 1.5 | 1.5 |
| | zinc carbonate | — | — | — | — | 0.5 | — | — | — | — | — |
| | aluminium hydroxide | — | — | — | — | — | — | — | 1.3 | 0.2 | — |
| (D) | polypropylene glycol with the molar mass of 2100 g/mol | — | — | — | 31.0 | — | 29.3 | 46.0 | — | 20.7 | 10.3 |
| | poly(ethylene, propylene) glycol with a molar mass of 3400 g/mol | 60.9 | 62.1 | 63.6 | 29.0 | 65.5 | 33.3 | 16.0 | 58.9 | 43.2 | 50.4 |
| (E) | diatomaceous earth | — | 5.3 | — | — | — | 10.8 | — | 12.7 | 1.4 | 18.3 |
| | precipitation silicic acid, hydrophobic, average particle size: 10 µm | 21.5 | 16.0 | 20.7 | 24.3 | 20.7 | 10.3 | 20.1 | 13.0 | 20.8 | 6.3 |

Suitability Test

One part by weight of each of the catalyst components K1 to K10 described in Table 1 were mixed with three parts by weight of the test substance: bisaziridino polyether with an imino equivalent mass of 3100 g/equivalent, prepared from a polyetherdiol which is composed of ethylene oxide and tetrahydrofuran units in the molar ratio 1:3.5.

In a period of three to five minutes the mixtures solidified to elastic materials at 23° C. which, after a storage time of 24 hours at room temperature, display a Shore A hardness of 50 to 70 measured according to DIN 53505.

All catalyst components according to the invention had a low acidity corresponding to the pH values given in Table 2, which were measured with a customary electrode from which a KCl solution emerged as electrolyte during the measurement.

The catalyst components according to the invention did not cause any skin irritation. Nor did damage of packaging plastics such as polyamide, polyoxymethylene diacetate or laminate film occur after 3 months' storage at 50° C. in contact with the catalyst components according to the invention.

TABLE 2

Acidity of the catalyst components according to the invention, determined as pH value

| Catalyst component according to Table 1 | pH-value |
| --- | --- |
| K1 | 4.6 |
| K2 | 4.4 |
| K3 | 4.2 |
| K4 | 3.6 |
| K5 | 3.2 |
| K6 | 4.1 |
| K7 | 4.5 |
| K8 | 2.2 |
| K9 | 3.7 |
| K10 | 4.6 |

Comparison Example

A catalyst component of the following composition was prepared.

| Constituent | Wt.-% |
| --- | --- |
| p-toluenesulphonic acid monohydrate | 9.9 |
| distilled water | 4.0 |
| precipitation silicic acid, hydrophobic average particle size: 10 μm | 20.8 |
| Poly(ethylene, propylene) glycol with a molar mass of 3400 g/mol | 65.3 |

The catalyst component had a very high acidity (pH-value of 0), displayed a caustic effect on the moist skin and damaged packaging plastics upon prolonged storage.

In addition, no processing times over 100 seconds could be achieved with this catalyst component, which is however necessary for a range of applications.

TABLE 3

Composition of the base component

| Constituent | Wt.-% |
| --- | --- |
| Mixture of bisaziridino polyethers with an average imino equivalent mass of 3190, prepared from a polyetherdiol which is composed of ethylene oxide and tetrahydrofuran units in the molar ratio 1:3.3 with a cyclic oligomeric polyether content of 0.2%. | 55.1 |
| Dibenzyl toluene (Jarytherm DBT, Elf Atochem) | 20.0 |
| Hydrogenated beef tallow (Ewanol HY2, Unichema) | 13.2 |
| Diatomaceous earth (Celatom MW 25, Chemag AG) | 11.7 |

TABLE 4

Characterization of the prepared mixtures of the catalyst components with the base component according to Table 2

| | Example No. | | | | | | | | | |
| --- | --- | --- | --- | --- | --- | --- | --- | --- | --- | --- |
| | 1 | 2 | 3 | 4 | 5 | 6 | 7 | 8 | 9 | 10 |
| Catalyst component used (according to TABLE 1) | K1 | K2 | K3 | K4 | K5 | K6 | K7 | K8 | K9 | K10 |
| Weight ratio: Catalyst component to base component | 1:5.2 | 1:4.9 | 1:5.0 | 1:6.0 | 1:5.1 | 1:5.0 | 1:4.5 | 1:5.0 | 1:4.0 | 1:5.3 |

TABLE 5

Processing behaviour and achieved shore A hardnesses of the preparations according to examples 1 to 10 (Table 4)

| | Example No. | | | | | | | | | |
| --- | --- | --- | --- | --- | --- | --- | --- | --- | --- | --- |
| Property | 1 | 2 | 3 | 4 | 5 | 6 | 7 | 8 | 9 | 10 |
| Processing time (23° C.) Seconds | 160 | 175 | 190 | 140 | 120 | 170 | 150 | 130 | 170 | 175 |
| Mouth-removal time Seconds | 270 | 285 | 330 | 300 | 315 | 280 | 260 | 240 | 300 | 290 |
| Shore A hardness after 24 hours according to DIN 53505 | 62 | 63 | 59 | 60 | 58 | 59 | 64 | 65 | 61 | 63 |

It can be seen from Table 1 in conjunction with Tables 4 and 5 that the molar ratio of the acids to the antacid compounds can be established by selection of the antacid compound, and the desired processing time by the water content. The mouth-removal time is also changed but, with use of the catalyst components according to the invention, lies in the range customary for precision modelling.

All mixtures of examples 1 to 10 according to the invention (Table 4) fulfilled the requirements for an elastic impression material in respect of breaking strength, elongation at break, permanent elastic deformation according to DIN/EN 24823, and led to shaped bodies which, after a storage time at room temperature of 24 hours, yielded a Shore A hardness (Table 5) well above 20.

All mixtures of examples 1 to 10 according to the invention (Table 4) yielded impressions which did not feel sticky after removal from the mouth and which were characterized by a very good design sharpness determined on appearance.

The individual components and also the mixtures did not display any unpleasant or noticeable odour.

The invention claimed is:

1. A catalyst component for a cationically curable composition comprising:
    (A) at least one Brönsted acid selected from the group consisting of hexafluoroantimonic acid, hexafluorophosphoric acid, tetrafluoroboric acid, sulfonic acids, phosphonic acids, polymeric acids, saturated carboxylic acids, unsaturated carboxylic acids, and reaction products of polyvalent alcohols and acid anhydrides,
    (B) water,
    (C) at least one antacid-acting compound which is an oxide, hydroxide, carbonate, or carboxylate of an element of aluminum, chromium, copper, germanium, manganese, lead, antimony, tellurium, titanium, or zinc,
    (D) at least one inert diluent, and
    (E) at least one modifier.

2. The catalyst component according to claim 1, comprising:
    (A) 0.1 to 50 wt.-% of at least one Brönsted acid,
    (B) 0.1 to 20 wt.-% of water,
    (C) 0.1 to 50 wt-% of at least one antacid-acting compound;
    (D) 0 to 95 wt.-% of at least one inert diluent,
    (E) 0 to 50 wt.-% of modifiers,
    wherein the wt-% data is related in each case to the overall mass of the catalyst component.

3. The catalyst component according to any one of the previous claims, comprising 0.5 to 2.0 base equivalents of the antacid-acting compound per acid equivalent of the Brönsted acid.

4. A catalyst component for a cationically curable composition comprising:
    (A) at least one Brönsted acid,
    (B) water,
    (C) at least one antacid-acting compound, wherein the antacid-acting compound is zinc oxide,
    (D) at least one inert diluent, and
    (E) at least one modifier.

5. A catalyst component for a cationically curable composition comprising:
    (A) at least one Brönsted acid selected from the group consisting of: arylsulphonic acids, alkylsulphonic acids, and alkylbenzenesulphonic acids,
    (B) water,
    (C) at least one antacid-acting compound which is an oxide, hydroxide, carbonate, or carboxylate of an element of aluminum, chromium, copper, germanium, manganese, lead, antimony, tellurium, titanium, or zinc,
    (D) at least one inert diluent, and
    (E) at least one modifier.

6. The catalyst component according to claim 4, wherein said Brönsted acid is p-toluenesulphonic acid or dodecylbenzenesulphonic acid.

7. The catalyst component according to claim 6, wherein the zinc oxide and the p-toluenesulphonic acid are in a molar ratio of 1:1.5 to 1:2.5.

8. A process for the preparation of a catalyst component for a cationically curable composition comprising:
    (A) at least one Brönsted acid selected from the group consisting of hexafluoroantimonic acid, hexafluorophosphoric acid, tetrafluoroboric acid, sulfonic acids, phosphonic acids, polymeric acids, saturated carboxylic acids, unsaturated carboxylic acids, and reaction products of polyvalent alcohols and acid anhydrides,
    (B) water,
    (C) at least one antacid-acting compound which is an oxide, hydroxide, carbonate, or carboxylate of an element of aluminum, chromium, copper, germanium, manganese, lead, antimony, tellurium, titanium, or zinc,
    (D) at least one inert diluent, and
    (E) at least one modifier,
the process comprising the steps of
    dissolving the Brönsted acid with water at 20° C. to 70° C. in a part of the inert diluent to form a solution, and
    adding a suspension of the antacid-acting compound to the solution.

9. A process for the preparation of a catalyst component for a cationically curable composition comprising:
    (A) at least one Brönsted acid selected from the group consisting of hexafluoroantimonic acid, hexafluorophosphoric acid, tetrafluoroboric acid, sulfonic acids, phosphonic acids, polymeric acids, saturated carboxylic acids, unsaturated carboxylic acids, and reaction products of polyvalent alcohols and acid anhydrides,
    (B) water,
    (C) at least one antacid-acting compound which is an oxide, hydroxide, carbonate, or carboxylate of an element of aluminum, chromium, copper, germanium, manganese, lead, antimony, tellurium, titanium, or zinc,
    (D) at least one inert diluent, and
    (E) at least one modifier,
the process comprising the steps of
    mixing constituents (A), (B), (D) and (E) to form a paste, and
    adding the antacid-acting compound.

10. The process according to claim 8, wherein the antacid-acting compound is added in the form of a paste or a suspension which was prepared from the antacid-acting compound and a part of the inert diluent.

11. A method for preparing a curable preparation, comprising the steps of mixing a catalyst component for a cationically curable composition together with a base component comprising an N-alkylaziridino-group-containing compound, the catalyst component comprising:
    (A) at least one Brönsted acid selected from the group consisting of hexafluoroantimonic acid, hexafluorophosphoric acid, tetrafluoroboric acid, sulfonic acids, phosphonic acids, polymeric acids, saturated carboxylic acids, unsaturated carboxylic acids, and reaction products of polyvalent alcohols and acid anhydrides,
    (B) water,
    (C) at least one antacid-acting compound which is an oxide, hydroxide, carbonate, or carboxylate of an element of aluminum, chromium, copper, germanium, manganese, lead, antimony, tellurium, titanium, or zinc,
(D) at least one inert diluent, and
(E) at least one modifier.

12. The method according to claim 11, wherein the weight ratio between the Brönsted acid and the N-alkylaziridino-group-containing compound is selected such that a ratio of an acid equivalent of the Brönsted acid to an imino equivalent of the N-alkylaziridino-group-containing compound is maintained at 1:0.5 to 1:5, preferably 1:1 to 1:3 and particularly preferably 1:1.2 to 1:2.0.

13. A two-component preparation comprising a catalyst component for a cationically curable composition and a base component which are separately stored, wherein the catalyst component comprises:
(A) at least one Brönsted acid selected from the group consisting of hexafluoroantimonic acid, hexafluorophosphoric acid, tetrafluoroboric acid, sulfonic acids, phosphonic acids, polymeric acids, saturated carboxylic acids, unsaturated carboxylic acids, and reaction products of polyvalent alcohols and acid anhydrides,
(B) water,
(C) at least one antacid-acting compound which is an oxide, hydroxide, carbonate, or carboxylate of an element of aluminum, chromium, copper, germanium, manganese, lead, antimony, tin, tellurium, titanium, or zinc,
(D) at least one inert diluent, and
(E) at least one modifier, and
wherein the base component comprises an aziridino polyether,
wherein said aziridino polyether has an average imino equivalent mass of 3100, and is preparable from a polyetherdiol which comprises ethylene oxide and tetrahydrofuran units in the molar ratio 1:3.5 solidifying within 0.5 to 20 minutes to a solid elastomer material which has a shore A hardness of at least 20 according to DIN 53505 after 24 hours storage time at room temperature.

14. A curable composition comprising:
(1) a catalyst component for a cationically curable composition comprising:
(A) a least one Brönsted acid selected from the group consisting of hexafluoroantimonic acid, hexafluorophosphoric acid, tetrafluoroboric acid, sulfonic acids, phosphonic acids, polymeric acids, saturated carboxylic acids, unsaturated carboxylic acids, and reaction products of polyvalent alcohols and acid anhydrides,
(B) water,
(C) at least one antacid-acting compound which is an oxide, hydroxide, carbonate, or carboxylate of an element of aluminum, chromium, copper, germanium, manganese, lead, antimony, tellurium, titanium, or zinc,
(D) at least one inert diluent, and
(E) at least one modifier, and
(2) a base component comprising N-alkylaziridino-group-containing compounds.

15. The curable composition according to claim 14, wherein the catalyst component comprises:
(A) 0.1 to 50 wt.-% of at least one Brönsted acid,
(B) 0.1 to 20 wt.-% of water,
(C) 0.1 to 50 wt.-% of at least one antacid-acting compound;
(D) 0 to 95 wt.-% of at least one inert diluent,
(E) 0 to 50 wt.-% of modifiers,
wherein the wt-% data is related in each case to the overall mass of the catalyst component.

16. The curable composition according to claim 14 or 15, wherein the catalyst component comprises 0.5 to 2.0 base equivalents of the antacid-acting compound per acid equivalent of the Brönsted acid.

17. The curable composition according to claim 14, wherein the antacid-acting compound is zinc oxide.

18. The curable composition according to claim 14, wherein said Brönsted acid is selected from the group consisting of: arylsulphonic acids, alkylsulphonic acids, and alkylbenzenesulphonic acids.

19. The curable composition according to claim 17, wherein said Brönsted acid is p-toluenesulphonic acid or dodecylbenzenesulphonic acid.

20. The curable composition according to claim 19, wherein the zinc oxide and the p-toluenesulphonic acid are in a molar ratio of 1:1.5 to 1:2.5.

21. A catalyst component for a cationically curable composition comprising:
(A) at least one Brönsted acid,
(B) water,
(C) at least one antacid-acting compound that is a zinc compound,
(D) at least one inert diluent, and
(E) at least one modifier.

22. The catalyst component of claim 21 wherein the antacid-acting compound is selected from the group consisting of zinc hydroxide, zinc oxide, zinc carbonate, and mixtures thereof.

23. The catalyst component of claim 1 wherein the at least one inert diluent is selected from the group consisting of polyether polyols, polyester polyols, polycarbonate diols, aliphatic esters, oils, fats, waxes, aliphatic hydrocarbons, araliphatic hydrocarbons, mono- or multifunctional esters of polyvalent acids, esters of alkylsulfonic acids, esters of arylsulfonic acids, amides of alkylsulphonic acids, and amides of arylsulphonic acids.

24. The catalyst component of claim 21 wherein the at least one inert diluent is selected from the group consisting of polyether polyols, polyester polyols, polycarbonate diols, aliphatic esters, oils, fats, waxes, aliphatic hydrocarbons, araliphatic hydrocarbons, mono- or multifunctional esters of polyvalent acids, esters of alkylsulfonic acids, esters of arylsulfonic acids, amides of alkylsulphonic acids, and amides of arylsulphonic acids.

25. The catalyst component of claim 1 wherein the at least one modifier is selected from the group consisting of fine-particle fillers, dyes, pigments, thixotropic agents, other additives influencing the flow behaviour, surfactants, odorous substances, and flavourings.

26. The catalyst component of claim 21 wherein the at least one modifier is selected from the group consisting of fine-particle fillers, dyes, pigments, thixotropic agents, other additives influencing the flow behaviour, surfactants, odorous substances, and flavourings.

27. A two-component preparation comprising a catalyst component for a cationically curable composition and a base component which are separately stored, wherein the catalyst component comprises:
(A) at least one Brönsted acid,
(B) water,
(C) at least one antacid-acting compound that is a zinc compound,
(D) at least one inert diluent, and
(E) at least one modifier, and wherein the base component comprises an aziridino polyether, wherein said aziridino polyether has an average imino equivalent mass of 3100, and is preparable from a polyetherdiol which comprises ethylene oxide and tetrahydrofuran units in the molar ratio 1:3.5 solidifying within 0.5 to 20 minutes to a solid elastomer material which has a shore A hardness of at least 20 according to DIN 53505 after 24 hours storage time at room temperature.

28. A curable composition comprising:
(1) a catalyst component for a cationically curable composition comprising:
 (A) a least one Brönsted acid,
 (B) water,
 (C) at least one antacid-acting compound that is a zinc compound,
 (D) at least one inert diluent, and
 (E) at least one modifier, and
(2) a base component comprising N-alkylaziridino-group-containing compounds.

* * * * *

UNITED STATES PATENT AND TRADEMARK OFFICE
CERTIFICATE OF CORRECTION

| | | |
|---|---|---|
| PATENT NO. | : 8,415,266 B2 | Page 1 of 1 |
| APPLICATION NO. | : 10/257760 | |
| DATED | : April 9, 2013 | |
| INVENTOR(S) | : Gunther Eckhardt | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1349 days.

Signed and Sealed this
First Day of October, 2013

Teresa Stanek Rea
*Deputy Director of the United States Patent and Trademark Office*